(12) United States Patent
Beatty

(10) Patent No.: US 6,764,984 B2
(45) Date of Patent: Jul. 20, 2004

(54) FLUORINATED LUBRICANT ADDITIVES

(75) Inventor: Richard P. Beatty, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 47 days.

(21) Appl. No.: 10/309,625

(22) Filed: Dec. 4, 2002

(65) Prior Publication Data
US 2003/0139300 A1 Jul. 24, 2003

Related U.S. Application Data

(63) Continuation of application No. 09/534,501, filed on Mar. 24, 2000, now Pat. No. 6,541,430.

(51) Int. Cl.[7] .................. C10M 137/06; C10M 137/04; C07F 9/02
(52) U.S. Cl. ...................... 508/435; 508/422; 508/431; 508/433; 558/86; 558/112; 558/183; 558/203; 558/204
(58) Field of Search ................................. 508/435, 433; 558/204

(56) References Cited

U.S. PATENT DOCUMENTS

| | | | |
|---|---|---|---|
| 2,959,544 A | * 11/1960 | Smith, Jr. et al. ........... | 508/371 |
| 3,124,533 A | 3/1964 | Metro et al. | |
| 3,284,355 A | 11/1966 | Papayannopoulos et al. | |
| 3,451,930 A | 6/1969 | Mead | |
| 3,763,282 A | * 10/1973 | Chance et al. .............. | 558/161 |
| 3,773,815 A | 11/1973 | Rossi | |
| 4,039,301 A | 8/1977 | Laity | |

(List continued on next page.)

FOREIGN PATENT DOCUMENTS

| | | |
|---|---|---|
| EP | 0125592 | 11/1984 |
| GB | 804777 | 11/1958 |
| GB | 874877 | 8/1961 |
| JP | 5815140 | 3/1983 |
| JP | 1122026 | 5/1989 |
| JP | 3-47317 | 7/1991 |
| JP | 7242584 | 9/1995 |
| JP | 8259482 | 10/1996 |
| JP | 8259501 | 10/1996 |
| JP | 2604186 | 1/1997 |
| SU | 449925 | 5/1975 |
| WO | WO 9310085 | 5/1993 |
| WO | WO 0065002 | 11/2000 |

OTHER PUBLICATIONS

J. Mater Chem, 1996, 6(6) pp. 917–918.
Lubr, Eng., Jul.–Aug. 1956, pp. 245–253.
Lubr. Eng., Jul.–Aug. 1956, pp. 245–253.
Chemical Abstracts, vol. 121, No. 24, Dec. 12, 1994, Columbus, Ohio, US; abstract No. 287485; Proyaev. V.V. et al, "Extraction of Group I–III Metals Using Fluorine Substituted Dithiophosphoric Acids in the Presence of the Crown Ethers 18K8 and 15K5"; XP002172857, Abstract & Radiokhimiya (1994), 36(2), 163–6.
Matus, L. I. et al., O,O–bis(1,1,3–trihydroperfluoropropyl)dithiophosphate esters; Journal of General Chemistry USSR., vol. 60, No. 11, Apr. 20, 1991, pp. 2218–2221, XP002172856, Consultants Bureau, New York, US.

Primary Examiner—Ellen M McAvoy
(74) Attorney, Agent, or Firm—Gerald E. Deitch

(57) ABSTRACT

Fluorinated dialkyl dithiophosphoric acids according to formula (I) and metallic salts thereof:

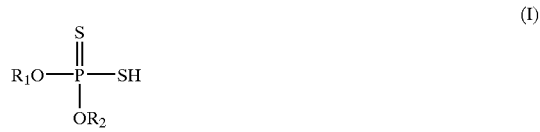

(I)

the compounds are useful, for example, as additives for lubricant compositions.

18 Claims, 3 Drawing Sheets

U.S. PATENT DOCUMENTS

| | | |
|---|---|---|
| 4,101,429 A | 7/1978 | Birke |
| 4,203,856 A | 5/1980 | Pardee |
| 4,308,154 A | 12/1981 | Clason et al. |
| 4,377,527 A | 3/1983 | Sabol et al. |
| 4,435,532 A | 3/1984 | Thormer et al. |
| 4,778,613 A | 10/1988 | Cherney et al. |
| 4,814,448 A | 3/1989 | Gatling et al. |
| 5,066,412 A | 11/1991 | Migdal et al. |
| 5,141,661 A | 8/1992 | DeRosa et al. |
| 5,152,908 A | 10/1992 | Tipton |
| 5,152,926 A | 10/1992 | Brown |
| 5,279,752 A | 1/1994 | Hasegawa et al. |
| 5,391,814 A | 2/1995 | Kai et al. |
| 5,510,513 A | 4/1996 | Kai et al. |
| 5,578,387 A | 11/1996 | Kai et al. |
| 5,641,731 A | 6/1997 | Baumgart et al. |
| 5,763,369 A | 6/1998 | Baumgart et al. |
| 5,962,377 A | 10/1999 | Baumgart et al. |
| 6,184,187 B1 * | 2/2001 | Howell et al. .............. 508/427 |
| 6,541,430 B1 * | 4/2003 | Beatty ....................... 508/368 |

* cited by examiner

FLUORINATED LUBRICANT ADDITIVES

This application in a continuation of application Ser. No. 09/534,501, filed Mar. 24, 2000, and now U.S. Pat. No. 6,541,430.

FIELD OF INVENTION

This invention relates to lubricant additives that provide anti-wear and friction-reducing properties when incorporated into lubricant compositions or other compositions where such properties are desired, such as motor oils.

BACKGROUND ART

A significant source of deterioration in machinery such as engines and motors that contain moving parts in mechanical motion at high temperatures is friction and wear between the contact surfaces of the moving parts. Such deterioration is particularly evident at startup and shutdown of the machinery. To combat these problems, lubricating agents such as lubricating oils, waxes and greases have traditionally been applied to the moving contact surfaces to prevent wear and to reduce friction.

Reducing or controlling friction is particularly important in motor oils, including automobile motor oils, because of the need to reduce wear, and also because this wear reduction must be accomplished while at the same time meeting standards for fuel economy as well as environmental vehicle fuel emissions control. Because of increased government regulation of vehicle fuel emissions, efforts have been made to improve engine performance, including improving engine design and emissions catalyst performance, as well as developing better additives such as lubricants and engine oil additives.

Ideally, a lubricant should provide lubrication of the entire contact surface. Such full-film contact is preferably achieved by completely coating the surfaces of the moving parts such that the parts never make contact. However, developing a full-film lubricant that is effective under the severe operating conditions of most engines and motors containing moving parts, has posed several difficulties. Design constraints, together with high load, slow speed, lubricant starvation, or low viscosity of the lubricant, may preclude full-film lubrication and increase the severity of contact. These conditions are often unavoidable during normal operation of machinery, and are particularly severe during startup and shutdown.

In cases where lubricants such as oils and greases cannot provide full-film lubrication at all times, anti-wear additives or friction modifiers are usually added. These anti-wear additives modify the surfaces to be lubricated through adsorption or chemical reaction to form coated surfaces that are characterized by reduced friction and increased wear resistance. It is generally recognized that different types of additives may interact in positive or negative ways and thereby enhance or interfere with each other's performance. Antiwear agents and friction modifiers in particular, because they are believed to function by modifying the rubbing surfaces through adsorption or chemical reaction, have a high probability of affecting each other's performance. This is because such materials adsorb on surfaces more or less strongly and compete with one another for surface adsorption sites. A strongly adsorbing material may exclude a more weakly adsorbing material from contact with the surface, thereby preventing it from exerting its effect on the surface. Such surface competition phenomena can pose significant challenges in developing additives and creating formulations where each additive can achieve its desired purpose.

Many kinds of anti-wear additives are known. In particular, organic phosphorus compounds such as dialkyl dithiophosphoric acids and dialkyl dithiophosphates have been used. Some of the most widely used and relied upon dialkyl dithiophosphates are metallic salts of dialkyl dithiophosphates, such as zinc dialkyldithiophosphates (ZDDPs), which find application in many different types of lubricants. The alkyl groups in zinc dialkyl dithiophosphates are typically derived from non-fluorinated alcohols that have been selected, based on chain length and degree of functional substitution, to impart desirable performance characteristics, such as solubility in the lubricant base fluid and thermal stability to the ZDDP. It is recognized that these characteristics can be changed by careful selection of the alkyl groups to optimize performance in particular applications.

ZDDP compositions are known to be effective in many formulations. This is evidence that they can compete very effectively for surface adsorption sites and thereby exert their effect on the rubbing surfaces. It might be predicted, therefore, that because ZDDPs adsorb strongly at surfaces and form very effective antiwear films by their chemical action at surfaces, such compounds would exclude other antiwear additives from adsorbing and exerting their effects at the surface.

Although ZDDPs have been used for many years in passenger car motor oil, their use is currently restricted because they contain phosphorus, and the amount of this element in motor oils is limited to less than 0.1%, since the phosphorus from ZDDP poisons catalytic converters, leading to increased vehicle emissions. It is anticipated that the future use of ZDDPs may be reduced even more than the current level. Anti-wear additives that can be used in place of ZDDPs, or in addition to them, are therefore of great interest.

ZDDPs have also been used in combination with certain molybdenum (Mo) additives, including soluble molybdenum additives such as molybdenum dialkyl dithiophosphates, molybdenum dialkyl dithiocarbamates and molybdenum amide complexes. One limitation of such ZDDP-Mo additive combinations, however, is that the molybdenum additives frequently reduce the anti-wear effectiveness of the ZDDPs, which is highly undesirable.

Other additives that may be included in lubricants as anti-wear additives include fluorinated organic compounds. Typical fluorinated compounds that may be used as lubricant additives include polytetrafluoroethylene (PTFE) and perfluoropolyether (PFPE). Fluorinated organic compounds, particularly esters and ethers, have been disclosed as lubricants for magnetic media, for example, in Japanese Patent 259482, Japanese Patent 08259501, and U.S. Pat. Nos. 5,578,387; 5,391,814 and 5,510,513.

Japanese Patent 01122026 teaches use of fluorine containing dibasic acid esters derived from diacids up to $C_8$ as lubricants for magnetic media. This publication, as does PCT publication, US/92/08331, teaches that the acid structure from which the diester is formed may have double bonds present. The molecular structures taught by each of these publications may also have fluorine atoms present in each of the end group.

Partly-fluorinated adipic acid diesters, $R_f(CH_2)_xO_2C(CH_2)_4CO_2(CH_2)_xR_f$, have been disclosed as lubricating coatings by Russian patent SU 449925. Bowers et al. (Lubr. Eng., July–August, 1956, pages 245–253) studied the boundary lubricating properties of several similar esters. The compounds disclosed in this publication have fluorine present in each of the diester groups, however the fluorination is symmetric. These symmetric, partially fluorinated esters have very low solubility in conventional lubricant base fluids and are therefore, of limited utility as additives in such base fluids.

Japanese Patent 2604186 discloses 1,2,3,4-butanetetracarboxylic acid tetraesters with partly-fluorinated alcohols, but since all four ester groups are derived from fluorinated alcohols, these esters, too, are symmetric. Other examples of the teaching of symmetrically fluorinated molecular structures include U.S. Pat. Nos. 4,203,856; 5,066,412 and 4,039,301 and in JP08259482 and JP08259501.

Fluorine-containing tri-carbonyl compounds, including some esters, are disclosed as lubricant additives in Japanese patent JP 07242584, and partial fluoroesters of polycarboxylic acids, in which the acid functional groups are not completely esterified was taught in U.S. Pat. No. 3,124,533.

Fluorinated organic compounds are thought to protect metal surfaces from wear by forming metal fluorides on the coated surfaces. Surface studies of coated metal surfaces suggest that the fluorinated organic compounds undergo tribochemical reactions, which are friction-stimulated chemical reactions, with the metal surfaces to form the metal fluoride. For example, in the case of a steel mechanism, the surfaces of which have been lubricated with PTFE, deposits of iron fluoride have been observed in the near-surface region of the wear region. Metal fluorides such as iron fluoride are known to have good properties as solid lubricants, and, accordingly, it is hypothesized that the metal fluoride formed by the interaction of the PTFE and the metal shears more readily than the metal itself, and is less prone to weld-fracture type of wear. As a result, use of the PTFE reduces friction and wear in the mixed and boundary lubrication regimes, where actual contact between the moving surfaces may occur.

Although fluorinated materials such as those described above have been used as lubricant additives, there are certain limitations to their usefulness in these applications. One limitation of these fluorinated materials is their very low solubility in conventional lubricant base fluids such as natural and synthetic hydrocarbons and esters, which has effectively limited their application to use as solid additives. Although solid additives may be used in lubricants, they pose several problems.

For example, highly fluorinated organic compounds used as lubricants are generally insoluble in most conventional lubricant base fluids. For example, the high degree of insolubility of perfluoropolyethers (PFPEs) makes it extremely difficult to use them as additives in lubricant formulations. While PFPEs themselves can be used as the lubricant base fluid, their high cost makes such a modification prohibitively expensive. Similar insolubility problems are characteristic of polytetrafluoroethylene (PTFE). PTFE, which is a mostly insoluble solid, can be finely dispersed as particles in lubricant base fluids to reduce friction and wear. However, effectiveness of such a dispersed solid lubricant depends on maintaining the PTFE particles in stable dispersion. Achieving an indefinitely stable dispersion is a challenge, particularly in a formulated lubricant, which may contain detergents, dispersants, or surfactants that may destabilize the PTFE dispersion. Moreover, solid particles in suspension are not very effective at forming films on the contact surfaces of mechanical parts, and this reduces the effectiveness of the tribochemical reactions that must occur at the metal surface to provide the desired lubricity. This is in direct contrast to liquid or soluble materials that may adsorb onto the metal surfaces for which they have affinity, thereby modifying those surfaces directly by participating in the surface chemical reactions that provide the lubricating effect. Particles of a dispersed solid may also flocculate in the lubricant over time. Such flocculated particles may then plug or restrict flow of the lubricant in the equipment and result in lubricant starvation in critical locations.

In view of the deficiencies in the art, it is an object of the present invention to provide a fluorinated lubricant additive which can serve as an anti-wear agent and friction reducer, and which, moreover, is compatible with conventional lubricant base fluids typically used in lubricant compositions. Desirably, such a lubricant additive should also overcome the cost and solubility limitations of previously known fluorinated organic compounds. This object has been achieved by the fluorinated compounds and compositions of the present invention.

DISCLOSURE OF INVENTION

The present invention provides fluorinated organic compounds according to formula (I), or metallic salts thereof:

(I)

wherein $R_1$ and $R_2$ are each independently selected from the group consisting of $C_1$ to $C_{40}$ organic residues; and wherein $R_1$ and $R_2$ are different, or $R_1$ and $R_2$ form a ring, and at least one of $R_1$ and $R_2$ is a fluorinated $C_1$ to $C_{40}$ organic residue.

Another embodiment of the invention comprises a compound of formula (I), or metallic salts thereof:

(I)

wherein $R_1$ and $R_2$ are each independently selected from the group consisting of $C_1$ to $C_{40}$ organic residues; and wherein $R_1$ and $R_2$ are the same or different, or $R_1$ and $R_2$ form a ring, and at least one of $R_1$ and $R_2$ is a fluorinated $C_1$ to $C_{40}$ organic residue, provided that when $R_1$ and $R_2$ are the same, neither $R_1$ nor $R_2$ can be $-(CH_2(CF_2)_xCF_2H)$, where x is 1, 3 or 5.

The invention further comprises an anti-wear additive comprising a compound of formula (I), or metallic salts thereof:

(I)

wherein $R_1$ and $R_2$ are each independently selected from the group consisting of $C_1$ to $C_{40}$ organic residues, or $R_1$ and $R_2$ form a ring; and wherein at least one of $R_1$ and $R_2$ is a fluorinated $C_1$ to $C_{40}$ organic residue.

The present invention also provides a process of making an anti-wear additive comprising:
a) preparing a mixture of two or more compounds, wherein said mixture includes at least one fluorinated compound and at least one non-fluorinated compound;
b) reacting the mixture with a thiophosphorus compound to form one or more oxygen linkages between the phosphorus atom of the thiophosphorus compound and each of the fluorinated and non-fluorinated compounds; and
c) recovering a fluorinated dithiophosphoric acid compound having the molecular structure according to formula (I):

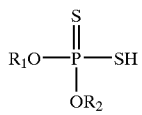
(I)

wherein $R_1$ and $R_2$ are each independently selected from the group consisting of fluorinated $C_1$ to $C_{40}$ organic residues; and
wherein $R_1$ and $R_2$ are different, or $R_1$ and $R_2$ form a ring.

When prepared in this way, the compounds of the present invention are generally produced in admixture with compounds where both $R_1$ and $R_2$ are fluorinated and with other compounds where both $R_1$ and $R_2$ are non-fluorinated. It is generally not necessary to separate or purify the compounds of the present invention when they are produced in such mixtures, and they may be used in that form in various applications.

The process of making anti-wear additives according to the invention may also include reacting the product of formula (I) with a source of metal atoms to form a metallic salt.

In yet another embodiment, the present invention includes a composition comprising a lubricant base fluid and one or more fluorinated anti-wear additives according to formula (I), and/or a metallic salt thereof, wherein $R_1$ and $R_2$ are each independently selected from the group consisting of $C_1$ to $C_{40}$ organic residues; and further wherein at least one of $R_1$ and $R_2$ is a fluorinated $C_1$ to $C_{40}$ organic residue.

MODE(S) OF CARRYING OUT THE INVENTION

Figure 1:
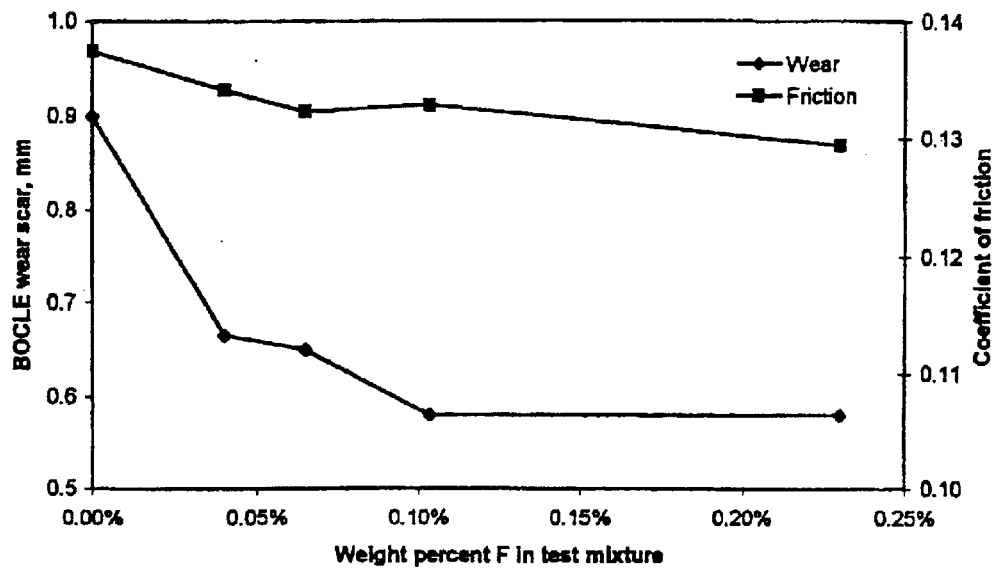
FIG. 1 shows ball-on-cylinder (BOCLE) performance of lubricant compositions containing non-fluorinated zinc dialkyl dithiophosphates (ZDDPs) in comparison to lubricant compositions containing the fluorinated zinc dialkyl dithiophosphates (F-ZDDPs) of the invention.

The present invention provides compounds useful as anti-wear additives that, may be used in lubricants, motor oils and other formulations where resistance to friction and deterioration caused by wear is desired. The compounds of the invention can also be used in any application where antioxidant properties are desired.

The compounds of the present invention include those represented by the molecular formula (I), and metallic salts thereof:

wherein $R_1$ and $R_2$ are each independently selected from the group consisting of $C_1$ to $C_{40}$ organic residues;
wherein $R_1$ and $R_2$ are the same or different, or $R_1$ and $R_2$ form a ring; and
wherein at least one of $R_1$ and $R_2$ is a fluorinated $C_1$ to $C_{40}$ organic residue.

The term "fluorinated", as it is used herein with respect to the organic residues, is intended to mean an organic compound containing one or more fluorine atoms. The term is also intended to include compounds including one or more $R_f$ groups, which are hydrocarbyl or hydrocarbyl-containing functional groups wherein one or more hydrogen substituents have been replaced by fluorine atoms. In this regard, the term "fluorinated" therefore also includes hydrocarbyl or hydrocarbyl-containing compounds, wherein only some hydrogen substituents have been replaced by fluorine atoms.

According to formula (I), above, either or both $R_1$ or $R_2$ may be derived from any fluorinated $C_1$ to $C_{40}$ organic residue possessing a functional group that is capable of reacting with the phosphorus atom to form an oxygen linkage. Such fluorinated organic residues may be comprised of hydrocarbyl groups or assemblies of hydrocarbyl groups, each of which may be optionally substituted or linked with atoms and/or functional groups that do not interfere with the reactions of the present invention. The hydrocarbyl groups, which may be fully or partially fluorinated, may be selected from straight chain, branched, or cyclic arrangements of one or more carbon atoms connected by single, double, triple, or aromatic bonds and substituted accordingly with hydrogen atoms, which may further be optionally substituted with functional groups or atoms that do not interfere with the chemistry of the present invention. Assemblies of hydrocarbyl groups, which may also be fully or partially fluorinated, comprise one or more such hydrocarbyl groups linked to other hydrocarbyl groups by carbon atoms or by linkages containing non-carbon atoms such as B, O, N, S, or P, and may include functional groups including, but not limited to ether, thioether, ester, thioester, borate ester, amide, amine, ketone and sulfoxide linkages. Oxygen (ether) linkages, designated herein as —OR, are preferred. These linkages may result in cyclic or heterocyclic structures, or may even conjoin $R_1$ and $R_2$ to form a cyclic moiety, such as a diol or polyol.

Preferably, the organic residue constituting $R_1$ or $R_2$ is derived from a fluorinated organic compound including one or more $R_f$ groups. Suitable fluorinated $C_1$ to $C_{40}$ organic residues used to form $R_1$ or $R_2$ may be selected from fluorinated alcohols. Most preferably, the fluorinated organic residue is a fluoroalkoxy group derived from a fluorinated primary, secondary or tertiary alcohol or phenol, wherein the alcohol or phenol has an alkyl, cycloalkyl or aryl backbone inclusive of one or more $R_f$ groups.

To form the —$OR_1$ and —$OR_2$ linkages in the compounds of formula (I), the fluorinated residues may be selected from fluorinated alcohols having the general molecular formula, $R_fOH$, and mixtures thereof, wherein the $R_f$ group is as defined above. Typically, a suitable fluorinated alcohol will comprise at least one spacer group between the —OH functionality of the alcohol and the fluorinated hydrocarbyl group, since alpha-fluoroalcohols, such as those containing a —$CF_2OH$ group, are reactively unstable. The spacer group is preferably, but not necessarily —$CH_2$. Accordingly, suitable fluorinated alcohols that may be used in the present invention may be selected from the following species:

$F(CF_2)_xCH_2OH$, wherein x is from 1 to about 20, such as 1H, 1H-heptafluoro-1-butanol and 1H, 1H-perfluoro-1-octanol;

$H(CF_2)_xCH_2OH$, wherein x is from 1 to about 20, such as 1H, 1H, 5H-octafluoro-1-pentanol;

$F(CF_2CF_2)_xCH_2CH_2OH$, wherein x is from 1 to about 10, such as 1H, 1H, 2H, 2H-perfluoro-1-octanol, and mixtures of perfluoroalkanols, examples of which are commercially available from DuPont Inc. under the tradename "ZONYL BA", having an average value of x of about 4.3, or "ZONYL BA-LD", which has an average value of x of about 3.7;

$F(CF_2CF_2)_x(CH_2CH_2O)_yOH$, a telomer ethoxylate alcohol wherein x is from 1 to about 10 and y is from 1 to about 20, which is preferably in the form of a mixture of such alcohols wherein the average value of x is about 3.9 and the average value of y is about 8;

$F(CFCF_3CF_2O)_xCF(CF_3)CH_2OH$, a poly hexafluoropropylene oxide (HFPO) alcohol wherein x is from 1 to about 20, which is preferably in the form of a mixture of such alcohols having an average value of x of about 6.7.

Regarding these alcohols, a mixture may be used. Such a mixture may contain one or more fluorinated alcohols of varying chain length and varying degrees of fluorination. For example, therefore, where a mixture of telomeric alcohols is used, minor amounts of longer-chain telomer alcohols may be present along with major amounts of shorter-chain telomer alcohols.

Preferred fluorinated alcohols for use in the invention may be selected from 1H, 1H, 2H, 2H-perfluoroalkanols having the molecular formula $F(CF_2CF_2)_xCH_2CH_2OH$, wherein x ranges from 1 to about 20. Most preferably, mixtures of 1H, 1H, 2H, 2H-perfluoroalkanols wherein x is from 1 to about 5 are preferred. An example of this type of alcohol is 1H, 1H, 2H, 2H-perfluoro-1-octanol.

The non-fluorinated $C_1$-$C_{40}$ organic residue may be comprised predominantly of hydrocarbyl groups or assemblies of hydrocarbyl groups, each of which may be optionally substituted or linked with atoms and/or functional groups that do not interfere with the reactions of the present invention. The hydrocarbyl groups may be selected from straight chain, branched, or cyclic arrangements of one or more carbon atoms connected by single, double, triple, or aromatic bonds and substituted accordingly with hydrogen atoms, which may further be optionally substituted with functional groups or atoms that do not interfere with the chemistry of the present invention, in particular halogen atoms. Assemblies of hydrocarbyl groups comprise one or more hydrocarbyl groups linked to other hydrocarbyl groups by carbon atoms or by linkages containing non-carbon atoms such as B, O, N, S, or P, and may include functional groups including, but not limited to ether, thioether, ester, thioester, borate ester, amide, amine, ketone and sulfoxide linkages. Oxygen (ether) linkages are preferred. These linkages may result in cyclic or heterocyclic structures, or may even conjoin $R_1$ and $R_2$ to form a cyclic moiety, such as a diol or polyol.

Any suitable non-fluorinated $C_1$ to $C_{40}$ organic residues may be used to form $R_1$ or $R_2$. Such residues may, for example, be selected from the group consisting of non-fluorinated alcohols, such that the non-fluorinated residue is an alkoxy group derived from the non-fluorinated alcohol, which forms an —OR, or —$OR_2$ linkage with the phosphorus atom. The non-fluorinated alcohol may be substituted such that it comprises an alkyl, cycoalkyl or aromatic backbone.

Exemplary non-fluorinated alcohols include, but are not limited to, primary, secondary and tertiary alcohols. Suitable primary alcohols include methanol, ethanol, 1-propanol, 1-butanol, and higher n-alkanols such as 1-octanol; and branched primary alcohols such as Oxo or Guerbet alcohols, for example, isotridecanol, which is commercially available under the tradename "EXXAL 13" from Exxon, 2-butyl octanol, which is commercially available under the tradename "ISOFOL 12" from Condea, or neopentyl alcohol. Suitable secondary alcohols include isopropanol, isobutanol, 4,4-dimethyl 2-pentanol, cyclohexanol, cyclododecanol, 2,6-dimethyl-4-heptanol, 3,7-dimethyl-3-octanol and 2-octanol. Suitable tertiary alcohols include t-butanol, and aryl alcohols such as phenol and cresol. The non-fluorinated alcohol may also be selected from diols and polyols such as ethylene glycol, propylene glycol, 1,4-butane diol, 1,5-pentane diol, 1,6-hexane diol, neopentyl glycol, trimethylol propane and pentaerythritol. Higher alcohols, such as plasticizers, detergents and fatty alcohols, all of which may be derived from known synthetic processes such as the Ziegler, Guerbet and Oxo processes, or by the hydrogenation of natural fats and oils, may also be used.

Either of the fluorinated or non-fluorinated compounds or both may be optionally substituted with functional groups that do not interfere in the reaction to form the desired oxygen linkages. For example, the respective components may contain ether linkages, such as in ethoxylated or propoxylated alcohols. They may also contain linear, branched or cyclic arrangements of atoms and may contain more than one branched groups that may be the same or different.

Preferably, at least one of $R_1$ or $R_2$ comprises a non-fluorinated residue, which may be any non-fluorinated $C_1$ to $C_{40}$ organic residue possessing a functional group that is capable of reacting with the phosphorus atom to form an oxygen linkage. In such an embodiment, the resulting fluorinated compounds of the invention may be non-symmetrically substituted with at least one fluorinated organic residue and at least one non-fluorinated organic residue. For example, a preferred compound according to formula (I) includes one fluorinated organic residue and one non-fluorinated organic residue as substituents.

As shown in formula (I), the fluorinated and non-fluorinated substituents $R_1$ and $R_2$ are bound to the phosphorus atom of a thiophosphorus compound by an R—O covalent single bond with an oxygen atom such that the compound of formula (I) are thiophosphorus compounds comprising at least one fluorinated substituent. Preferably, in formula (I), where $R_1$ is a fluorinated substituent, $R_2$ is a non-fluorinated substituent.

Any suitable thiophosphorus compound may be reacted with the fluorinated and non-fluorinated compound to form the fluorinated anti-wear additives of the invention. In the reaction to form the compounds of the present invention, the phosphorus atom may be supplied by reacting a thiophosphorus compound with at least one fluorinated compound and at least one non-fluorinated compound to form one or more R—O covalent bonds between the phosphorus atom and each of the fluorinated and non-fluorinated compounds.

Suitable thiophosphorus compounds include thiophosphoryl halides and thiophosphoryl anhydrides. The reaction between the fluorinated compounds, non-fluorinated compounds and the thiophosphorus compound produces a substituted thiophosphoric acid or derivative thereof, according to formula (I). Preferably, the thiophosphorus compound is selected from the group consisting of thiophosphoric anhydrides. Most preferably, the thiophosphorus compound is phosphorus pentasulfide, which is available commercially, for example, from Aldrich Chemical Company, catalog number 23,210–6.

Preferably, the reaction is conducted between a thiophosphoric acid anhydride, $P_2S_5$, a $C_1$–$C_{40}$ fluorinated alcohol and a $C_1$–$C_{40}$ non-fluorinated alcohol, thereby forming a dialkyl dithiophosphoric acid compound, which is substituted with at least one fluorine-containing substituent and at least one non-fluorine containing substituent.

The fluorinated compounds of the present invention may be prepared, for example, by first reacting the thiophosphorus compound with a limited, less than stoichiometric amount of a fluorinated reactant, and then reacting the product of the first reaction with a non-fluorinated reactant to complete formation of compounds according to formula (I). Alternatively, a non-fluorinated reactant may be reacted first, followed by a non-fluorinated reactant, to form compounds of formula (I). In another alternative, a mixture of at least one fluorinated reactant and at least one non-fluorinated reactant, which is preferably a mixed-isomer, long-chain, non-fluorinated compound, may be reacted with the thiophosphorus compound in a single step. The proportions of the fluorinated and non-fluorinated reactants in the combination of reactants used to make the compounds of the invention may vary, depending on the specific fluorinated and non-fluorinated reactants that are selected. The reactants are selected to incorporate sufficient fluorine to provide the resulting compounds with the desired anti-wear effect, yet retain compatibility with the intended use application. For example, where the use application is a lubricant composition, the compounds should contain a proportion of fluorine that renders them compatible with the lubricant base fluid. Typically, the proportion of fluorinated reactant is from about 1 mole % to about 50 mole % of the combined reactants. Additives containing between about 2% weight and 25% weight of fluorine are preferred.

The reaction used to form the oxygen linkages between the fluorinated and non-fluorinated compounds and the phosphorus atom may be selected from any of the reaction methods known in the art. In some cases particular reaction methods may be more favorable because of rate, and or the ability to remove unwanted byproducts such as hydrogen sulfide, which is toxic and malodorous. Preferably, the dialkyl dithiophosphoric acids and salts thereof of this invention are prepared by the reaction of a mixture comprising at least one fluorinated compound comprising one or more $R_f$ groups, and at least one non-fluorinated compound, with a thiophosphorus compound.

In a particularly preferred embodiment, one or more fluorinated alcohols, one or more non-fluorinated alcohols and phosphorus pentasulfide are reacted together to form a dialkyl dithiophosphoric acid compound as the product. Both the fluorinated alcohols and the non-fluorinated alcohols of the present invention may be further substituted with other functional groups, provided that the added substituents do not interfere with either the reaction with phosphorus pentasulfide to form the dialkyl dithiophosphoric acid, or with any subsequent reaction to form the metallic salt.

In such a preferred embodiment, the substituents $R_1$ and $R_2$ may each be different in that at least one of these substituents is fluorinated and the other is non-fluorinated. The resulting dialkyl dithiophosphoric acid compound is therefore non-symmetrical. Such non-symmetrical compounds are advantageous in that the presence of the fluorinated substituent provides enhanced tribochemical friction-reducing and wear-reducing performance when the compound is used, for example, in a lubricant additive. At the same time, the presence of the non-fluorinated substituent improves the solubility of the compound in typical lubricant base fluids.

The dialkyl dithiophosphoric acids may be further converted into metallic dialkyl dithiophosphate salts. In this regard, the dialkyl dithiophosphoric acids are reacted with a metal or metallic compound to promote conversion to the dithiophosphoric acid salt. Any suitable metal or metallic compound that will form an oil-soluble or oil-dispersible salt may be used. Suitably, the metal is an alkali metal, an alkali earth metal or a transition metal. For example, the source of metal atoms may be a metal or metallic compound of zinc, molybdenum, barium, aluminum, calcium, lithium, lead, tin, copper, cadmium, cobalt, strontium, nickel, or combinations thereof. Preferably, the metal atom is derived from zinc, molybdenum or compounds thereof. Most preferably, the metal atom is derived from zinc metal or from zinc salts including, but not limited to, zinc acetate, zinc oxide and zinc hydroxide.

The process of making the metallic salts according to the invention includes combining the product of formula (I) with a pure metal or metallic compound, such as a metallic salt, to cause a reaction forming the metallic dialkyl dithiophosphoric acid salt. If desired, this reaction may be accelerated by heating, for example at reflux temperature. The basis of the reaction is the neutralization of one or more dialkyl dithiophosphoric acids with a basic metallic compound or metal to form a salt. The salt derived from this reaction comprises a metal atom covalently or ionically linked to one or more dialkyl dithiophosphoric acid residues, the number of acid residues depending on the valency of the metal atom. In this respect, the molecular structure of the salt may vary from being a simple binary salt to being a coordination complex having multiple dialkyl dithiophosphoric acid residues coordinated to the metal atom. Generally, the molecular structure of a binary salt according to the invention may be represented by the formula (II):

$$[M^{x+}][S(S)P(OR)_2]_x \qquad (II)$$

wherein x is the valency of the metal atom, and the R groups are selected from $R_1$ and $R_2$, as defined above, provided that at least one of $R_1$ or $R_2$ is fluorinated. An example of this type of salt is fluorinated sodium dialkyl dithithiophosphate, represented by the formula $Na[S(S)P(OR)]_2$. Transition metal atoms, which have higher valencys, may form higher molecular weight salts. For example, one fluorinated molybdenum compound that may be formed according to the reaction may be represented as:

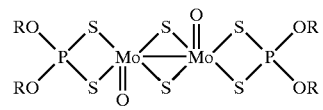

wherein the R groups may be any of $R_1$ and $R_2$, as defined above, provided that at least one of $R_1$ or $R_2$ is fluorinated. The degree of substitution of the metal atom with the acid residues may also depend on the stoichiometry of the reaction. According to these factors therefore, numerous possible metallic salts may be formed.

A typical zinc dialkyl dithiophosphoric acid salt which may be formed according to the invention may be represented by the formula:

$$[Zn^{2+}][S(S)P(OR)_2]_2 \quad (III)$$

To form the dithiophosphate salt, a pure metal or metallic salt is added to the reaction mixture containing one or more dialkyl dithiophosphoric acids of formula (I), and the resulting mixture is stirred and optionally heated to promote neutralization to the salt, represented as formula (III). For example, fluorinated zinc dialkyl dithiophosphates may be prepared using zinc acetate, according to the scheme:

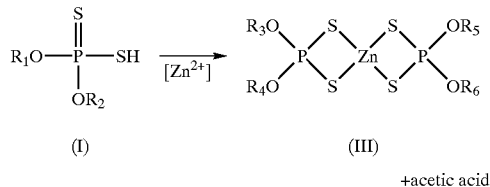

+acetic acid wherein $R_1$ and $R_2$ of formula (I) are as defined above, and $R_3$, $R_4$, $R_5$ and $R_6$ of formula (III) are $C_1$–$C_{40}$ fluorinated or non-fluorinated organic residues. Where the substituents $R_1$ and $R_2$ are fluorinated or non-fluorinated, as desired the resulting zinc dialkyl dithiophosphates of formula (III) may comprise those same substituents as either of $R_3$, $R_4$, $R_5$ or $R_6$.

In the formation of zinc dialkyl dithiophosphates according to the invention, several sources of the metal atom may be used to provide the active metal ion species, however different by-products may be formed as a result of the neutralization reaction.
Possible zinc sources and the resulting by-products may include:

| [M] | By-product | Active species |
| --- | --- | --- |
| ZnO | $H_2O$ | $Zn^{2+}$ |
| $Zn(OH)_2$ | $H_2O$ | $Zn^{2+}$ |
| Zn metal | $H_2O$ | $Zn^{2+}$ |
| $Zn(OAc)_2$ | acetic acid | $Zn^{2+}$ |

Similar by-products would be expected where the active species is selected from other suitable metal ions, as described and exemplified herein.

The degree of fluorine substitution in the fluorinated dialkyl dithiophosphates may vary according to the degree of initial substitution in the compounds of formula (I) and the completeness of the reaction between the fluorinated and unfluorinated residues with the thiophosphoryl compound. Additionally, depending on the position of the fluorinated substituents in the compounds of formula (I), one or more metallic salts according to formula (II) may be formed, resulting in a mixed product. This mixed product may also include unreacted dialkyl dithiophosphoric acids in combination with the metallic salt derivatives. Although usually not necessary, if desired, the mixed products of the present invention may be purified by centrifugation, distillation, fractional crystallization, filtration, extraction, or other standard methods known to those skilled in the art. For example, the dithiophosphate product may be dissolved in a solvent and less soluble impurities may be removed by filtration. Examples of suitable solvents for this purpose are cyclohexane, toluene or mineral oils. The resulting product is typically a viscous liquid or waxy solid at room temperature.

The non-symmetrical substitution that may be seen in the dialkyl dithiophosphoric acids may also occur in the dithiophosphate salts formed by neutralization of the acids. Such substitution provides the same benefits in terms of wear performance and solubility to the resulting dithiophosphate products. Accordingly, the non-symmetrical dialkyl dithiophosphoric acids and dialkyl dithiophosphates of the invention demonstrate heightened performance both in terms of preventing or reducing wear and with respect to their solubility in lubricating compositions.

Fluorinated metal dithiophosphate salts, and in particular, fluorinated zinc dialkyl dithiophosphate salts (F-ZDDPs) according to this invention have been found to be useful anti-wear additives in lubricating compositions such as lubricants and motor oils. Moreover, when the zinc dialkyl dithiophosphate salts of the present invention are included in a lubricant base oil, the resulting composition is much more effective at reducing wear than the base oil alone. It has surprisingly been discovered that the fluorinated zinc dialkyl dithiophosphates of the present invention exhibit superior anti-wear properties in comparison to related non-fluorinated zinc dialkyl dithiophosphoric acids or dithiophosphates. Accordingly, use of F-ZDDPs may enable formulation of passenger car motor oil (PCMO) lubricants with reduced phosphorus content, which would reduce phosphorus poisoning of emissions catalysts. It has also been found that F-ZDDP function at least similarly to, or better than non-fluorinated ZDDPs, in combination with molybdenum additives useful in low-friction PCMO or other low-friction lubricant formulations.

Additionally, in contrast to conventional fluorinated additives, the at least partially fluorinated F-ZDDPs of the present invention are soluble and compatible with conventional lubricant base fluids such as mineral oils, polyalphaolefins and esters. Conventional fluorinated lubricants, such as polytetrafluoroethylene (PTFE) or perfluoroethers (PFPE), are typically highly fluorinated, are of high molecular weight and are insoluble in oils. For example, PTFE, a conventional fluorinated lubricant, contains a fully fluorinated carbon chain, and has a molecular proportion of fluorine ranging from 68% to 76% by weight. In contrast, the F-ZDDPs of the invention preferably comprise from about 1% by weight to about 50% by weight of fluorine, preferably from about 1% by weight up to about 30% by weight. It has been observed that even a very small amount of the fluorinated alcohol component can impart dramatic wear and friction reducing benefits when F-ZDDPs are used as additives in lubricant formulations. The presence of a non-fluorinated alcohol component further enhances the performance of the F-ZDDPs of the invention. In particular, the non-fluorinated alcohol component of the preferred F-ZDDPs increases solubility such that they are quite soluble in oils, and reduces cost, compared to F-ZDDPs prepared solely from fluorinated alcohols.

The function of F-ZDDPs as anti-wear lubricant additives presents surprising improvements over the use of other conventionally known fluorinated compounds. ZDDPs, because of their ability to adsorb strongly to metal wear surfaces, would predictably prevent other types of anti-wear additives from exerting any surface-modifying effect. It is therefore surprising that incorporation of fluorinated substituents to form F-ZDDPs very significantly improves the performance of these compounds in relation to nonfluorinated ZDDPs. It is further surprising that these dramatic improvements demonstrated by F-ZDDP performance can be obtained using only minor amounts of fluorinated substituents in combination with major amounts of nonfluorinated substituents.

The lubricant compositions of the invention may be prepared by dissolving the fluorinated additives in a suitable lubricant base fluid. Any suitable lubricant base fluid may be used. Preferably, the lubricant base fluid has a viscosity grade such as might be used for blending of an oil in an internal combustion engine. The viscosity of the base oil depends on the lubricant application and may vary over a wide range. The range may be from ISO 10 to ISO 1000, or even higher or lower. For motor oils, the viscosity of the base fluid is suitably in the range of from ISO 10 to ISO 150. One example of a suitable lubricant base fluid is "HYDROCLEAR®", a hydrocracked mineral base oil fluid having an ISO viscosity of 32, which contains no additives.

The lubricant compositions can also include one or more other conventionally known lubricating or anti-wear additives, such as completely non-fluorinated metal dialkyl dithiophosphates. For example, various molybdenum dithiophosphates available commercially under the tradename "MOLYVAN" from R.T. Vanderbilt Co. may be added to the compositions. One such compound is molybdenum, bis[O, O-bis(2-ethylhexyl) phosphorodithioato-S,S'] dioxodi-mu-thioxodi-, (Mo—Mo), available commercially as "MOLYVAN-L". Other soluble molybdenum compounds useful in lubricant compositions are available from Asahi Denka under the tradename "ADEKA SAKURALUBE".

The additives of the invention may also be used in combination with other known anti-wear additives, such as non-fluorinated ZDDPS and non-fluorinated molybdenum anti-wear additives, including molybdenum dialkyl dithiophosphates, molybdenum dialkyl dithiocarbamates and molybdenum amide complexes. The non-fluorinated molybdenum additives, which are known to reduce the effectiveness of non-fluorinated ZDDPs, do appear to have an adverse effect on wear performance of F-ZDDPs as well, however because F-ZDDPs offer better wear performance than non-fluorinated ZDDPs, F-ZDDPs may be used with molybdenum additives and still retain excellent anti-wear performance in comparison to the use of non-fluorinated ZDDPs and molybdenum additives.

The fluorinated additives can be used in desired amounts to give the desired results. For example, when used in motor oils, the amount of additive can range from about 0.1% by weight to about 10% by weight, based on the weight of the motor oil.

The anti-wear additives of the invention may be combined with other conventional ingredients in a lubricant or passenger car motor oil (PCMO) formulation. A viscosity modifier may be added. Suitable viscosity modifiers include, but are not limited to, olefin copolymers such as NORDEL®, polymethacrylates and others. Additionally, one or more conventional ingredients selected from the group consisting of oxidation inhibitors, pour point depressants, detergents, dispersants, friction modifiers, anti-wear agents, foam inhibitors, corrosion inhibitors and metal deactivators may also be included. Suitably, viscosity modifiers are added to a PCMO at a concentration ranging from about 4% to about 15% by weight, while other additives described above may be constitute from about 3% to about 15% by weight, although the amounts required to produce the desired effect in the compositions of the present invention would be readily apparent to one skilled in the art.

The following examples illustrate the present invention, but are not intended to be limiting.

EXAMPLES

Fluorinated anti-wear additives of the invention were prepared and evaluated to determine their performance as anti-wear agents. $^{31}$P chemical shifts were calculated based on spectrometer operating parameters and represent the approximate chemical shift, in ppm, downfield of external $H_3PO_4$.

Example 1

Preparation of zinc bis [Di-(25 mole % ZONYL BA, 75 mole % 2-octyl)-dithiophosphate] using zinc acetate In a glovebox, a 250-ml 3-necked round bottom flask was charged with 5.56 g phosphorus pentasulfide, $P_2S_5$ (Aldrich), to provide a concentration of 25 mmol. About 10 ml toluene was used to rinse the $P_2S_5$ down the neck and walls of the flask. The flask was capped with rubber septa. In a fume hood, a slow counter-flow of dry nitrogen was introduced from a needle inserted through one of the rubber septa, and the flask was fitted with a dropping funnel containing a charge of 10.74 g 2-octanol (82.5 mmol), a reflux condenser and a magnetic stir bar. The outlet of the reflux condenser was connected via a plastic tubing to a caustic scrubber, then vented to the hood.

A mixture of 13.2 g ZONYL BA (27.5 mmol), which is a mixture of perfluorinated alcohols, and 20 ml toluene was warmed in a water bath to melt and dissolve the perfluorinated alcohol, then this mixture was added in one portion to the reaction flask. 2-octanol was then added via the dropping funnel over 6 minutes, while the reaction mixture was heated, using a heating mantle, from an initial temperature of 47° C. at the time of addition of the warm toluene and perfluorinated alcohol mixture, to a temperature of 52° C. The mixture was then heated to reflux for about 2.3 hours at a temperature of 110° C. to 115° C. At the end of the reaction, the $P_2S_5$ had completely dissolved, and an off-white product was formed that appeared to be more viscous than the product formed in reactions without the fluorinated alcohol, which instead produced a clear, green-tinted product. $^{31}$P NMR (Nuclear Magnetic Resonance) spectra showed three major signals at chemical shifts of 83.9, 85.9 and 87.9 ppm, which were assigned to di-2-octyl dithiophosphoric acid, the mixed ZONYL BA-octyl dithiophosphoric acid and di-ZONYL BA dithiophosphoric acid, respectively. From the integration of the NMR signal, it was evident that the relative proportions of these three compounds in the mixture was that which was statistically predicted, based on the relative amounts of fluorinated alcohol and 2-octanol used in the preparation.

The reaction mixture was then cooled to 28° C., after which 5.05 g of a solid, anhydrous zinc acetate (27.5 mmol) was added in a single portion. This mixture was refluxed at a temperature of 110° C. to 115° C. for approximately 3 hours. The product was filtered while warm at a temperature of about 60° C., and the filter rinsed with toluene. The resulting air-dried filter cake weighed 0.1011 g. The filtrate was stripped in vacuo to yield 27.47 g of zinc dialkyl dithiophosphate at 90% of the theoretical yield.

The $^1$H and $^{31}$P NMR spectra of the zinc bis[di-(25 mole % ZONYL BA, 57 mole % 2-octyl)-dithiophosphate] were determined. The spectra showed that the proportion of 2-octyl and fluorinated alcohol substituents in the dithiophosphate were consistent with the proportions expected from the starting alcohol mixture of 25% fluorinated alcohol and 75% 2-octanol.

Examples 2–6

Additional fluorinated zinc dialkyl dithiophosphates were prepared using different combinations of fluorinated compounds, non-fluorinated compounds and zinc sources, and using phosphorus pentasulfide ($P_2S_5$) as the thiophosphorus compound. Each sample was prepared analogous to the methodology described for Example 1. The combination and proportions of the reactants, and the resulting product F-ZDDP of Examples 2–6, as well as Example 1 are detailed in Table 1, below:

TABLE 1

| Example | F-ZDDP Product | Fluorinated compound/ (weight) | Non-fluorinated compound/ (weight) | Zinc source (grams) |
|---|---|---|---|---|
| 1 | Zinc bis[di-25 mole % ZONYL BA, 75 mole % 2-octyl) dithiophosphate] | ZONYL BA 13.2 g | 2-octanol 10.74 g | Zinc acetate 5.05 g |
| 2 | Zinc bis[di-2.5 mole % ZONYL BA, 97.5 mole % 2-octyl) dithiophosphate] | ZONYL BA 1.32 g | 2-octanol 13.97 g | Zinc acetate 5.05 g |
| 3 | Zinc bis[di-5 mole % ZONYL BA, 95 mole % 2-octyl) dithiophosphate] | ZONYL BA 2.64 g | 2-octanol 13.61 g | Zinc acetate 5.05 g |
| 4 | Zinc bis[di-10 mole % ZONYL BA, 90 mole % 2-octyl) dithiophosphate] | ZONYL BA 5.28 g | 2-octanol 12.89 g | Zinc acetate 5.05 g |
| 5 | Zinc bis[di-25 mole % ZONYL BA-LD, 75 mole % 2-octyl) dithiophosphate] | ZONYL BA-LD 11.44 g | 2-octanol 10.74 g | Zinc acetate 5.05 g |
| 6 | Zinc bis[di-25 mole % ZONYL BA, 75 mole % isotridecanol) dithiophosphate] | ZONYL BA 13.2 g | EXXAL 13 (isotridecanols) 16.34 g | Zinc acetate 5.05 g |

Comparative Example A

Preparation of non-fluorinated ZDDP, zinc bis(Di-2-octyl-dithiophosphate)

In a glovebox, a 250 ml 3-necked round bottom flask was charged with 5.56 g $P_2S_5$ (25 mmol) and 30 g toluene. The flask was capped with rubber septa and placed in a fume hood. Under a slow counter-flow of nitrogen from a needle inserted through one of the rubber septa, the flask was fitted with a dropping funnel containing 14.33 g 2-octanol (110 mmol), a reflux condenser and a magnetic stir bar. The outlet of the reflux condenser was connected via a plastic tubing to a caustic scrubber, then vented to the hood.

The 2-octanol was added over 11 minutes without external heating, after which the reaction temperature exothermically rose from 28° C. to 33° C. The reaction mixture was then heated using a heating mantle and refluxed at a pot temperature of approximately 115° C. for about 2 hours, after which time all the $P_2S_5$ had dissolved. The reaction mixture was clear and green. $^{31}P$ NMR in deuterobenzene showed one major signal at 83.9 ppm. This signal was assigned to 2-octyl dithiophosphoric acid.

After cooling the reaction mixture, an excess of 3.6 grams of zinc dust (55 mmol, 2.2×theoretical concentration) was added in one portion. The mixture was stirred, heated and held at reflux for about 2 hours. The mixture was cooled, then filtered through a 0.2 micron Millipore® filter. The residual Zn left behind on the filter was rinsed with toluene, then air-dried. The recovered weight of the air-dried, unused zinc was 2.09 g. The filtrate and toluene rinses were combined and stripped in vacuo, using a full-pump vacuum, to remove toluene. The product was a clear liquid of a pale blue-green color at a recovered weight of 19.68 g, which was essentially a quantitative yield. $^1H$ and $^{31}P$ NMR were consistent with the molecular structure of the product.

Comparative Example B

Preparation of non-fluorinated ZDDP, zinc bis(di-isotridecyl dithiophosphate

This comparative example was prepared using the preparation scheme as for Comparative Example A, except that 21.78 g of an isotridecanol mixture, available commercially under the tradename "EXXAL 13" from Exxon Chemical Company, was used as the non-fluorinated alcohol, and in the initial reaction, only 30 g the toluene solvent was used, all of which was added to the reaction vessel before the isotridecanol was added.

The following test methods were used to evaluate representative samples according to the present invention.
Test Methods Samples were tested using the ball-on-cylinder (BOCLE) test over a 30 minute test period, as described in ASTM D5001. Several modifications were made to the test, which are summarized in Table 2. These changes were made to make the test a more severe test of anti-wear and friction-modifying properties. Wear was determined according to ASTM D5001, and was quantified by the size of the wear scar on the ball, as measured at the end of the testing period. Using this test, a smaller wear scar indicated less wear. The coefficient of friction was calculated from the ratio of the tangential (lateral) force on the ball to the downward (normal) force on the ball. For each determination of this parameter, the reported measurement was the average value during the final 26 minutes of the test period, with the first 4 minutes allowed for break-in. In all cases, the normal force was 12,000 grams.

TABLE 2

Ball-on-cylinder test conditions

| Standard ASTM D5001 | Modified D5001 (consequence) |
|---|---|
| 0.5" ball | 0.25" ball (smaller contact area) |
| 25° C. | 80° C. (lower lubricant viscosity) |
| 1000 g load, 30 minutes | 500 g break in load, 0.5 minute, followed by 6000 g test load, 30 minutes (higher contact pressure; note that a 6000 g load produces a 12,000 g normal force at the ball-cylinder contact point) |

TABLE 2-continued

Ball-on-cylinder test conditions

| Standard ASTM D5001 | Modified D5001 (consequence) |
|---|---|
| No friction data | Calibrated load cell to measure tangential force on ball during test (allows calculation of coefficient of friction from ratio of tangential force to normal force, 12,000 g) |

The relative performance of the materials of the present invention as additives in HYDROCLEAR®, a commonly available, high-quality, hydrocracked mineral oil from Conoco, was evaluated. The grade of HYDROCLEAR which was used, ISO 32 viscosity grade, is a grade which might be used as one component for blending of oil for use in an internal combustion engine. HYDROCLEAR ISO 32 base oil contains no additives.

HYDROCLEAR ISO 32 base oil was tested according to the modified BOCLE method numerous times. The average of these results is summarized in Table 3.

TABLE 3

HYDROCLEAR ISO 32 Oil BOCLE results

| Solvent-refined 150N oil | Coefficient of friction | Wear scar, mm |
|---|---|---|
| Number of measurements | 16 | 16 |
| Average | 0.1314 | 0.905 |
| Standard deviation | 0.0052 | 0.030 |
| 95% Confidence interval | ±0.0028 | ±0.016 |

To determine the efficacy of the additives of the invention in reducing friction and wear, these parameters were measured as a function of the concentration of F-ZDDP, made according to the invention, in the hydrocracked ISO 32 oil. The F-ZDDPs were prepared to have a constant molar concentration of phosphorus in each sample.

For comparative purposes, the friction and wear performance of several commercially available passenger car motor oils formulated according to the International Lubricant Standardization and Approval Committee (ILSAC) GF-1 and GF-2 standards were measured. The GF-1 oils tested included two leading full synthetics, "MOBIL 1 5W30" and Castrol "SYNTEC 5W50", and one conventional non-synthetic oil, "MOTORCRAFT 5W30". Performance of all three oils was very similar, as is summarized in Table 4. This may be because all three contained similar amounts of zinc dialkyldithiophosphate (ZDDP), an extremely effective anti-wear agent. The GF-2 oils tested were from Castrol®, Valvoline®, Pennzoil®, Mobil®, Conoco® and Quaker State®, and represented viscosity grades 5W30, 10W30, 10W40, 5W50 and 20W50.

The level of phosphorus (P) from ZDDPs in GF-1 motor oils is typically about 0.12% (1200 ppm). The current GF-2 motor oils contain only 0.1% P and future generations of oil are expected to contain even less P. Lower P has adversely affected wear performance, as seen in Table 4.

TABLE 4

Commercially Available Motor Oil BOCLE Test Results

| BOCLE Parameters | GF-1 Motor Oil | | GF-2 Motor Oil | |
|---|---|---|---|---|
| | Coefficient of friction | Wear scar, mm | Coefficient of friction | Wear scar, mm |
| Number of measurements | 2 | 9 | 32 | 32 |
| Average | 0.1313 | 0.499 | 0.1281 | 0.544 |
| Standard deviation | 0.0029 | 0.029 | 0.0146 | 0.060 |
| 95% Confidence interval | ±0.0260 | ±0.022 | 0.0053 | 0.022 |

These results indicate that the current standard GF-2 motor oil, even containing a conventional anti-wear additive, has a higher coefficient of friction resulting in a larger wear scar, and is therefore less effective at preventing wear.

To determine the efficacy of the additives made according to the present invention, their effect on friction and wear was measured as a function of their concentration in HYDROCLEAR ISO 32 oil. Generally, there are two approaches to obtaining a given level of fluorine in a blended lubricant. An additive containing a high level of fluorine can be used at a low treat rate or an additive containing a low level of fluorine can be used at a high treat rate. These two approaches do not necessarily give the same performance.

The accompanying figures graphically demonstrate the superior performance of the fluorinated anti-wear additives of the invention. FIG. 1 shows BOCLE performance for the ZDDP of Comparative Example A and the F-ZDDPs of Examples 1–4. As seen in Table 1, these compounds were prepared from various mixtures of ZONYL BA and 2-octanol, wherein the molar percentage of ZONYL BA was varied from zero to 25%. Each of the samples were tested at a concentration of the additive that would yield a level of about 500 ppm phosphorus, P, in the test fluid. It was observed that as the amount of ZONYL increased from zero (Comparative Sample A) to about 25 mole percent (Example 1), the amount of fluorine, F, increased from zero to 23 mole %. According to FIG. 1, there was a dramatic reduction of BOCLE wear scar diameter from about 0.9 mm to about 0.6 mm. All the F-ZDDP samples showed less wear than the non-fluorinated ZDDP of Comparative Example A.

Figure 2:
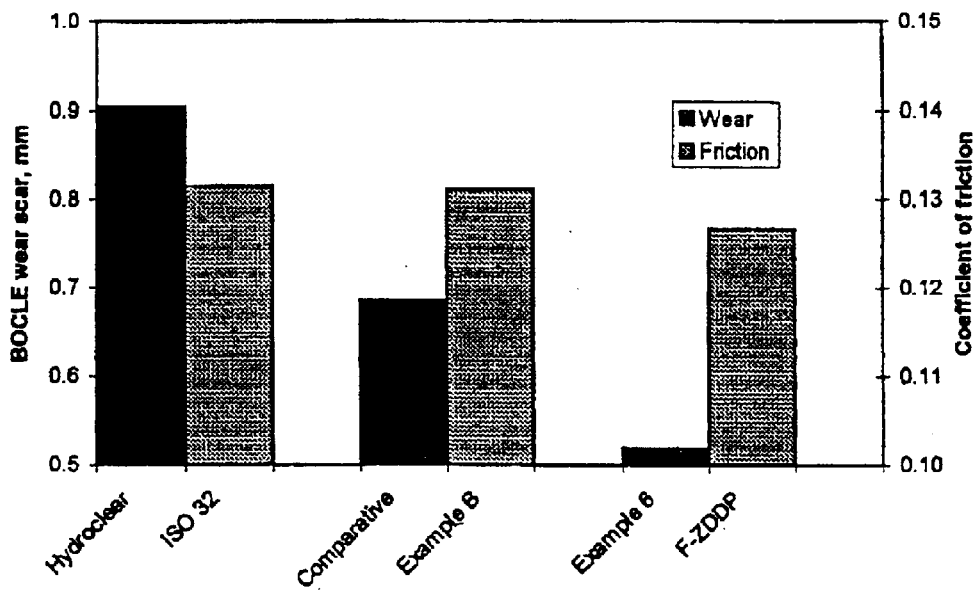
FIG. 2 shows BOCLE performance of lubricant compositions containing ZDDPs in comparison to lubricant compositions containing the F-ZDDPs of the invention.

FIG. 2 shows BOCLE performance for the ZDDP of Comparative Example B, prepared from isotridecanol, and the F-ZDDP of Example 6. Both samples were tested in HYDROCLEAR ISO 32 mineral oil at a concentration sufficient to yield a phosphorus concentration of 500 ppm P. The performance of the mineral oil alone, as a control test, is also shown. It is clear from FIG. 2 that using the F-ZDDP formed from the combination of ZONYL and isotridecanol caused dramatically lower wear than use of a ZDDP prepared from isotridecanol alone (Comparative Example B).

Figure 3:
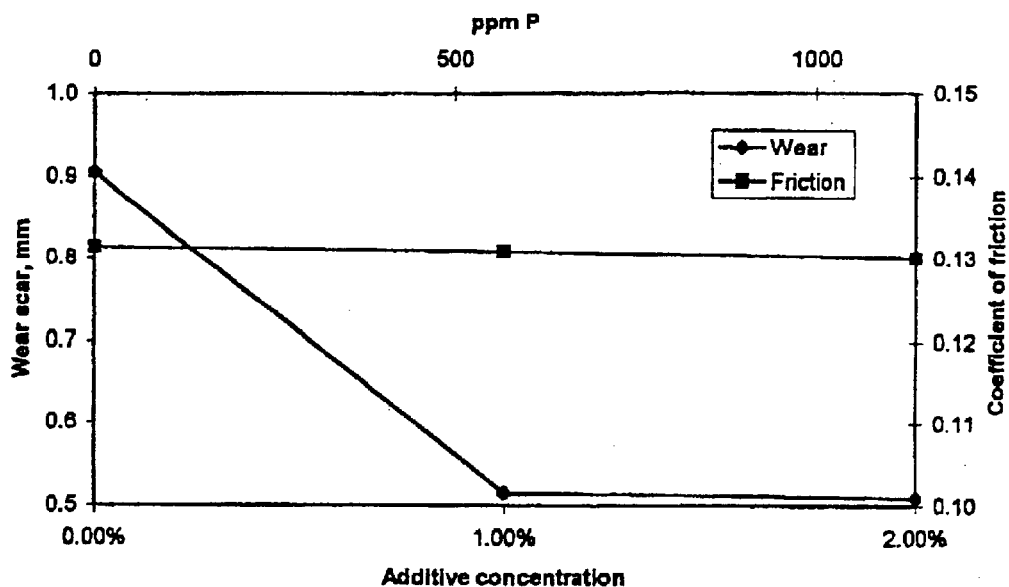
FIG. 3 shows BOCLE wear performance of a lubricant composition containing an F-ZDDP according to the invention.
Figure 4:
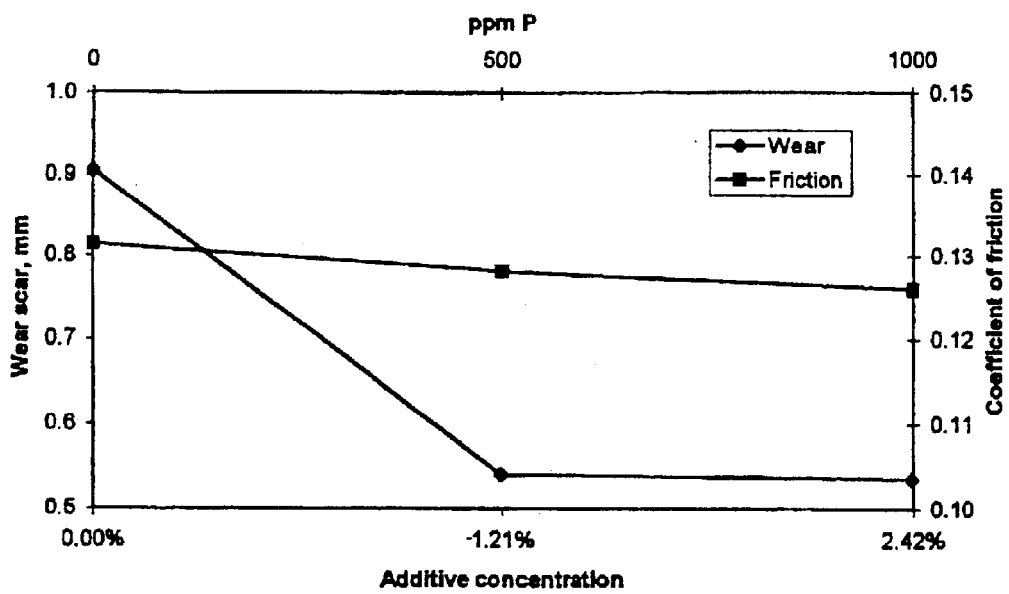
FIG. 4 shows BOCLE wear performance of a lubricant composition containing an F-ZDDP according to the invention.

FIG. 3 and FIG. 4 show the BOCLE performance of F-ZDDP from Examples 5 and 6, respectively. It was observed that, even at low concentrations, these additives caused a dramatic reduction of the BOCLE wear scar diameter from about 0.9 mm to from about 0.5 to 0.6 mm.

Figure 5:
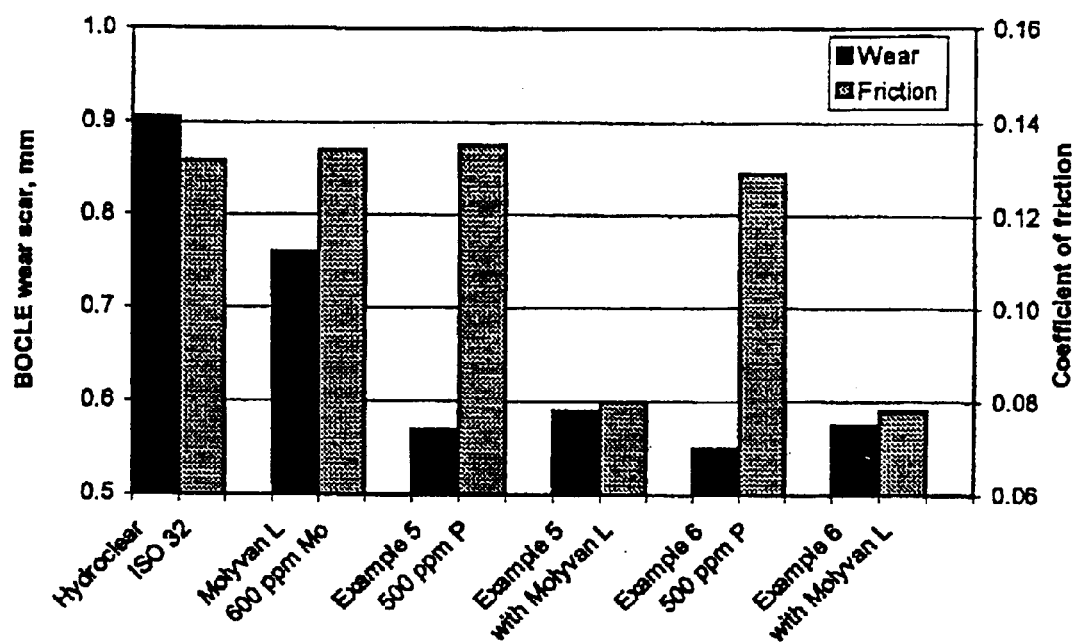
FIG. 5 illustrates the low-friction synergy between an F-ZDDP of the present invention and a molybdenum dialkyl dithiophosphate.

FIG. 5 illustrates the low friction synergy between an F-ZDDP of the present invention and a commercially available molybdenum dialkyl dithiophosphate, MOLYVAN L at 600 ppm (about 0.7% weight). HYDROCLEAR mineral oil alone was evaluated as a control test.

Elemental analysis using standard analytical procedures was also performed for each of metallic salts of Examples 1–6 and Comparative Examples A and B. These analyses were extremely difficult due to multiple interferences. Accordingly, $CeCl_3$, $Ag_2O$ and cation exchange resins were used to remove P and S interference when determining the molar percentage of F. The molar percentage of each element, as well as the calculated molar percentage is set forth in Table 5:

TABLE 5

| Example | Carbon Wt. % (theoretical wt. %) | Hydrogen Wt. % (theoretical wt. %) | Phosphorus Wt. % (theoretical wt. %) | Sulfur Wt. % (theoretical wt. %) | Flourine Wt. % (theoretical wt. %) | zinc Wt. % (theoretical wt. %) |
|---|---|---|---|---|---|---|
| Comp. Ex. A | 51.12 (49.76) | 9.02 (8.87) | 8.54 (8.02) | 16.84 (16.60) | | 7.83 (8.46) |
| Comp. Ex. B | 60.3 (59.31) | 10.30 (10.34) | 6.49 (5.88) | 11.65 (12.18) | | 6.67 (6.21) |
| 1 | 37.9 (36.19) | 5.40 (4.73) | 6.26 (5.28) | 12.84 (10.94) | 28.77 (31.83) | 6.88 (5.58) |
| 2 | 48.78 (47.93) | 8.66 (8.32) | 7.53 (7.82) | 12.63 (15.87) | 6.11 (4.19) | 9.20 (8.09) |
| 3 | 47.44 (46.26) | 7.53 (7.82) | 6.56 (7.35) | 15.67 (15.21) | 8.56 (8.02) | 8.95 (7.75) |
| 4 | 44.53 (43.31) | 7.21 (6.93) | 10.82, 6.25[a] (6.78) | 12.88, 7.97 (14.03) | 14.00, 6.57[a] (14.80) | 8.59 (7.15) |
| 5 | 38.95 (37.50) | 5.45 (5.24) | 5.69 (5.86) | 10.03 (12.12) | 22.76 (27.07) | 6.72 (6.18) |
| 6 | 46.38 (43.71) | 6.42 (6.20) | 4.14 (4.48) | 7.81 (9.27) | 19.83 (26.98) | 5.49 (4.73) |

[a]replicate sample

This data reflected the basic characterization of the compounds of the invention, and established their molecular composition as fluorinated dialkyl dithiophosphates.

Additional fluorinated zinc dialkyl dithiophosphates and comparative examples of non-fluorinated zinc dialkyl dithiophosphates were prepared according to the following schemes:

Comparative Example C

Dicyclododecyl dithiophosphoric acid and zinc salt from cyclododecanol

In the glovebox, a 250 mL 3-necked round-bottom flask was charged with 5.56 g $P_2S_5$ (25 mmol). About 10 mL toluene was used to rinse $P_2S_5$ down from the neck and walls of the flask. The flask was capped with rubber septa and brought out into the hood. Under a slow counter-flow of dry nitrogen from a needle inserted through one of the rubber septa, the flask was fitted with a dropping funnel containing 20.28 g cyclododecanol (110 mmol), a cyclic alcohol, and 30.42 g toluene, which had been warmed to dissolve the cyclododecanol, reflux condenser, and magnetic stir-bar. The outlet of the reflux condenser was connected via plastic tubing to a caustic scrubber, then vented to the hood.

The solution of cyclododecanol in toluene was added via the dropping funnel, over 21 minutes, while the reaction mixture was heated with the heating mantle from ambient temperature to 105° C. The reaction was heated to reflux (118–120° C.) and held for about 1.4 hours, at which time $P_2S_5$ had dissolved, giving a clear, green solution. $^{31}P$ NMR showed the major signal to be at 85.0 ppm, assigned to dicyclododecyl dithiophosphoric acid.

After cooling the reaction mixture to 37° C., solid, anhydrous zinc acetate (5.05 g, 27.5 mmol, Aldrich) was added in one portion. The mixture was heated to reflux for about 2 hours. The product was filtered while warm (about 60° C.), and the filter rinsed with toluene. The air-dried filter cake weighed 0.1641 g. The filtrate was stripped in vacuo at about 50° C. to yield the product as a sticky, glassy mass. Elemental analysis, $^1H$, and $^{31}P$ NMR spectra were consistent with the expected product ZDDP composition. The $^{31}P$ NMR spectrum showed the major signal to be at 93.7 ppm, assigned to the zinc salt of dicyclododecyl dithiophosphoric acid.

Comparative Example D

Dicyclohexyl dithiophosphoric acid and zinc salt from cyclohexanol

In the glovebox, a 250 mL 3-necked round-bottom flask was charged with 5.56 g $P_2S_5$ (25 mmol) and 20 mL toluene. The flask was capped with rubber septa and brought out into the hood. Under a slow counter-flow of dry nitrogen from a needle inserted through one of the rubber septa, the flask was fitted with a dropping funnel containing 11.02 g cyclohexanol (110 mmol), reflux condenser, and magnetic stir-bar. The outlet of the reflux condenser was connected via plastic tubing to a caustic scrubber, then vented to the hood.

The cyclohexanol was added via the dropping funnel, over 3 minutes, while the reaction mixture was heated with the heating mantle from ambient temperature to 42° C. The reaction was heated to reflux (114–116° C.) and held for about 1 hour, at which time $P_2S_5$ had dissolved, giving a clear, green solution. $^{31}P$ NMR showed the major signal to be at 83.1 ppm, assigned to dicyclohexyl dithiophosphoric acid.

After cooling the reaction mixture to 29° C., solid, anhydrous zinc acetate (5.05 g, 27.5 mmol, Aldrich) was added in one portion. The mixture was heated to reflux (108–111° C.) for about 2 hours. The product was filtered while warm (about 60° C.), and the filter rinsed with toluene. The air-dried filter cake weighed 0.18 g. The filtrate was stripped in vacuo at about 50° C. to yield the product as an off-white solid. Elemental analysis, $^1H$, and $^{31}P$ NMR spectra were consistent with the expected product ZDDP composition. The $^{31}P$ NMR spectrum showed the major signal to be at 93.7 ppm, assigned to the zinc salt of dicyclohexyl dithiophosphoric acid.

Comparative Example E

Preparation of di-2-octyl dithiophosphoric acid and zinc salt by neutralization with ZnO In the glovebox, a 250 mL 3-necked round-bottom flask was charged with 5.56 g $P_2S_5$, 25 mmol, and 30 g cyclohexane. The flask was capped with rubber septa and brought out into the hood. Under a slow counter-flow of dry nitrogen from a needle inserted through one of the rubber septa, the flask was fitted with a dropping funnel (containing 14.33 g 2-octanol, 110 mmol), reflux condenser, and magnetic stirbar. The outlet of the reflux condenser was connected via plastic tubing to a caustic scrubber, then vented to the hood.

The 2-octanol was added over 7 minutes while the reaction was heated from ambient temperature to 37° C. using a heating mantle. The reaction was heated at reflux (pot temperature approx. 83–87° C.) for approx. 5 hours, at which time all $P_2S_5$ had dissolved. The reaction mixture was clear and green. $^{31}P$ NMR showed one major signal at 83.9 ppm, assigned to the di-2-octyl dithiophosphoric acid.

After cooling the reaction mixture, 2.03 g ZnO (25 mmol) was added in one portion. The mixture was stirred, heated, and held at reflux for 7.5 hours. The product was cooled, then filtered through a 0.2 micron Millipore filter. The white solid retained by the filter, presumably unreacted ZnO, was rinsed with cyclohexane, then air-dried (0.2 g). The filtrate and cyclohexane rinses were combined and stripped in vacuo to remove cyclohexane. The product was a clear liquid with a pale blue-green color (18.3 g, 95% of theoretical yield). Elemental analysis 1H, and 31P NMR data were consistent with the expected ZDDP composition. The major signal at about 95 ppm was assigned to Zinc(II) bis(di-2-octyldithiophosphate).

Example 7

Mixed cyclododecyl-ZONYL BA dithiophosphoric acid and zinc salt from a mixture of cyclododecanol and ZONYL BA In the glovebox, a 250 mL 3-necked round-bottom flask was charged with 5.56 g $P_2S_5$ (25 mmol). About 10 mL toluene was used to rinse $P_2S_5$ down from the neck and walls of the flask. The flask was capped with rubber septa and brought out into the hood. Under a slow counter-flow of dry nitrogen from a needle inserted through one of the rubber septa, a solution of 1.23 g ZONYL BA (3 mmol) in 10 g toluene, which had been warmed mildly to dissolve the ZONYL BA, was added in one portion, then the flask was fitted with a dropping funnel containing 19.77 g cyclododecanol (107 mmol), and 29.66 g toluene, which had been warmed to dissolve the cyclododecanol), reflux condenser, and magnetic stir-bar. The outlet of the reflux condenser was connected via plastic tubing to a caustic scrubber, then vented to the hood.

The solution of cyclododecanol in toluene was added via the dropping funnel, over 11 minutes, while the reaction mixture was heated with the heating mantle from ambient temperature to 80° C. The reaction was heated to reflux (118–120° C.) and held for about 1.5 hours, at which time $P_2S_5$ had dissolved, giving a clear, green solution. $^{31}P$ NMR showed the major signal to be at 84.6 ppm, assigned to dicyclododecyl dithiophosphoric acid. A smaller signal at 86.2 ppm, which was about 2.4% the intensity of the major signal, was assigned to the mixed cyclohexyl-ZONYL dithiophosphoric acid.

After cooling the reaction mixture to 60° C., 5.05 g of solid, anhydrous zinc acetate (27.5 mmol, Aldrich ) was added in one portion. The mixture was heated to reflux (103–113° C.) for about 2 hours. The product was filtered while warm (about 60° C.), and the filter rinsed with toluene. The air-dried filter cake weighed 0.46 g. The filtrate was stripped in vacuo at about 50° C. to yield the product as a sticky, taffy-like mass. Elemental analysis, $^1H$, and $^{31}P$ NMR spectra were consistent with the expected product ZDDP composition. The $^{31}P$ NMR spectrum showed the major signal to be at 93.7 ppm, assigned to the zinc salt of dicyclododecyl dithiophosphoric acid, consistent with Comparative Example C. A smaller signal at 96.4 ppm was assigned to the zinc salt of the mixed cyclododecyl-ZONYL dithiophosphoric acid. The normalized integrated intensities of the two signals were 96% and 4%, very close to the 95% and 5% statistically expected from the mixture of alcohols used in the preparation.

Example 8

Mixed cyclohexyl-ZONYL BA dithiophosphate and zinc salt from a mixture of cyclohexanol and ZONYL BA In the glovebox, a 250 mL 3-necked round-bottom flask was charged with 5.56 g $P_2S_5$ (25 mmol) and 35 g toluene. The flask was capped with rubber septa and brought out into the hood. Under a slow counter-flow of dry nitrogen from a needle inserted through one of the rubber septa, a solution of 1.32 g ZONYL BA (2.75 mmol) in 15 g toluene, which had been warmed mildly to dissolve the ZONYL BA, was added in one portion, then the flask was fitted with a dropping funnel (containing 10.74 g cyclohexanol, 107.25 mmol), reflux condenser, and magnetic stir-bar. The outlet of the reflux condenser was connected via plastic tubing to a caustic scrubber, then vented to the hood.

The cyclohexanol was added via the dropping funnel, over 6 minutes, while the reaction mixture was heated with the heating mantle from ambient temperature to about 63° C. The reaction was heated to reflux (115–117° C.) and held for about 1.4 hours, at which time $P_2S_5$ had dissolved, giving a clear, green solution. $^{31}P$ NMR showed the major signal to be at 82.3 ppm, assigned to dicyclohexyl dithiophosphoric acid. A smaller signal at 84.7 was assigned to the mixed cyclohexyl-ZONYL dithiophosphoric acid.

After cooling the reaction mixture to 29° C., solid, anhydrous zinc acetate (5.05 g, 27.5 mmol, Aldrich ) was added in one portion. The mixture was heated to reflux (111–112° C.) for about 2 hours. The product was filtered while warm (about 60° C.), and the filter rinsed with toluene. The air-dried filter cake weighed 0.30 g. The filtrate was stripped in vacuo at about 50° C. to yield the product as an off-white solid. Elemental analysis, $^1H$, and $^{31}P$ NMR spectra were consistent with the expected product ZDDP composition. The $^{31}P$ NMR spectrum showed the major signal to be at 93.9 ppm, assigned to the zinc salt of dicyclohexyl dithiophosphoric acid. A smaller signal at about 97.5 ppm was assigned to the zinc salt of the mixed cyclohexyl-ZONYL dithiophosphoric acid, but both signals were too broad for accurate integration.

Examples 9–12

Examples 9 and 10 were prepared analogously to Example 7, except using the alcohols and quantities listed in Table 6. Examples 11 and 12 were prepared as for Example 8 except using the alcohols and quantities listed in Table 6. All dialkyldithiophosphoric acids were characterized by $^1H$ and $^{31}P$ NMR, and were determined to be consistent with the expected compositions. All zinc salt products were characterized by elemental analysis, $^1$H, and $^{31}$P NMR, and were determined to be consistent with the expected compositions.

Example 13

In the glovebox, a 250 mL 3-necked round-bottom flask was charged with 5.56 g P$_2$S$_5$ (25 mmol) and 30 g toluene. The flask was capped with rubber septa and brought out into the hood. Under a slow counter-flow of dry nitrogen from a needle inserted through one of the rubber septa, the flask was fitted with a dropping funnel (containing 12.89 g 2-octanol, 99 mmol, and 4.01 g 1H,1H,2H,2H-perfluorooctanol, 11 mmol), reflux condenser, and magnetic stir-bar. The outlet of the reflux condenser was connected via plastic tubing to a caustic scrubber, then vented to the hood.

The mixture of alcohols was added via the dropping funnel, over 11 minutes, while the reaction mixture was heated with the heating mantle from ambient temperature to about 93° C. The reaction was heated to reflux (119–120° C.) and held for about 0.6 hours, at which time P$_2$S$_5$ had dissolved, giving a clear, green solution. $^{31}$P NMR showed the major signal to be at 83.9 ppm, assigned to di-2-octyl dithiophosphoric acid. A smaller signal at 85.9 was assigned to the mixed nonfluorinated-2-octyl—fluorinated-octyl dithiophosphoric acid and an even smaller signal at 87.8 was assigned to di-fluorinated-octyl dithiophosphoric acid.

After cooling the reaction mixture to 38° C., solid, anhydrous zinc acetate (5.05 g, 27.5 mmol, Aldrich) was added in one portion. The mixture was heated to reflux (111–113° C.) for about 2 hours. The product was filtered while warm (about 60° C.), and the filter rinsed with toluene. The air-dried filter cake weighed 0.25 g. Solvent was removed from the filtrate in vacuo at about 50° C. to yield the product as a yellow liquid. Elemental analysis, $^1$H, and $^{31}$P NMR spectra were consistent with the expected product ZDDP composition. The $^{31}$P NMR spectrum showed the major signal to be at 93.9 ppm, assigned to the zinc salt of di-2-octyl dithiophosphoric acid. A smaller signal at about 97.9 ppm was assigned to the zinc salt of the mixed fluorinated-nonfluorinated dithiophosphoric acid, and a still smaller signal at about 102.9 ppm was assigned to the zinc salt of the di-fluorinated alcohol dithiophosphoric acid. The integrated intensities of these three broad signals were 73:21:6, in reasonable agreement with the intensities expected statistically from the mixture of alcohols used in the preparation (81:18:1).

Examples 14–17

Examples 14 through 17 were prepared using the method used to prepare Example 13, except that the fluorinated alcohols and quantities were used as listed in Table 6. All dialkyldithiophosphoric acids were characterized by $^1$H and $^{31}$P NMR, which were consistent with the expected compositions. All zinc salt products were characterized by elemental analysis, $^1$H, and $^{31}$P NMR, which were consistent with the expected compositions.

TABLE 6

| Example | Nonfluorinated alcohol | Fluorinated alcohol | Molar proportion of fluorinated alcohol: nonfluorinated alcohol |
| --- | --- | --- | --- |
| Comparative Example C | Cyclododecanol, 20.28 g, 110 mmol | none | 0:1 |
| Comparative Example D | Cyclohexanol, 11.02 g, 110 mmol | none | 0:1 |
| Comparative Example E | 2-Octanol, 14.33 g, 110 mmol | none | 0:1 |
| Example 7 | Cyclododecanol, 19.77 g, 107.25 mmol | ZONYL BA, 1.32 g, 2.75 mmol | 0.025:0.975 |
| Example 8 | Cyclohexanol, 10.74 g, 107.25 mmol | ZONYL BA, 1.32 g, 2.75 mmol | 0.025:0.975 |
| Example 9 | Cyclododecanol, 19.26 g, 104.5 mmol | ZONYL BA, 2.64 g, 5.5 mmol | 0.05:0.95 |
| Example 10 | Cyclododecanol, 18.25 g, 99 mmol | ZONYL BA, 5.28 g, 11 mmol | 0.1:0.9 |
| Example 11 | Cyclohexanol, 10.47 g, 104.5 mmol | ZONYL BA, 2.64 g, 5.5 mmol | 0.05:0.95 |
| Example 12 | Cyclohexanol, 9.92 g, 99 mmol | ZONYL BA, 5.28 g, 11 mmol | 0.1:0.9 |
| Example 13 | 2-Octanol, 12.89 g, 99 mmol | 1H,1H,2H,2H-perfluorooctanol, 4.01 g, 11 mmol | 0.1:0.9 |
| Example 14 | 2-Octanol, 12.89 g, 99 mmol | 1H,1H,5H-octafluoropentanol, 2.55 g, 11 mmol | 0.1:0.9 |
| Example 15 | 2-Octanol, 12.89 g, 99 mmol | 1H,1H-heptafluorobutanol, 2.20 g, 11 mmol | 0.1:0.9 |
| Example 16 | 2-Octanol, 12.89 g, 99 mmol | 1H,1H-perfluorooctanol, 4.4 g, 11 mmol | 0.1:0.9 |
| Example 17 | 2-Octanol, 12.89 g, 99 mmol | 1H,1H,9H-perfluorononanol, 4.75 g, 11 mmol | 0.1:0.9 |

The following examples show formation of fluorinated dialkyl dithiophosphate salts using various metal sources, such as sodium hydroxide, calcium carbonate, molybdenum acetate, zinc hydroxide and copper carbonate. It will be apparent to those skilled in the art that other metal compounds can be similarly used to prepare salts from fluorinated dialkyl dithiophosphoric acids according to the present invention.

Example 18

A mixed cyclododecyl-ZONYL dithiophosphoric acid is prepared similarly to Example 7. The acid is neutralized by addition of zinc hydroxide (2.73 g, 27.5 mmol). The product salt is isolated by solvent removal in vacuo.

Example 19

A mixed cyclododecyl-ZONYL dithiophosphoric acid is prepared similarly to Example 7. The acid is neutralized by addition of molybdenum (II) acetate (5.9 g, 27.5 mmol Mo equivalent). The product salt is isolated by solvent removal in vacuo.

Example 20

A mixed cyclododecyl-ZONYL dithiophosphoric acid is prepared similarly to Example 7. The acid is neutralized by addition of sodium hydroxide (2.2 g, 55 mmol). The product salt is isolated by solvent removal in vacuo.

Example 21

A mixed cyclododecyl-ZONYL dithiophosphoric acid is prepared similarly to Example 7. The acid is neutralized by addition of calcium carbonate (2.75 g, 27.5 mmol). The product salt is isolated by solvent removal in vacuo.

Example 22

A mixed cyclododecyl-ZONYL dithiophosphoric acid is prepared similarly to Example 7. The acid is neutralized by addition of basic copper carbonate (3.04 g, 27.5 mmol Cu equivalent). The product salt is isolated by solvent removal in vacuo.

I claim:

1. A compound according to formula (I) or metallic salts thereof:

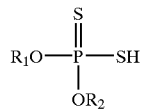

(I)

wherein $R_1$ and $R_2$ are each independently selected from the group consisting of $C_1$ to $C_{40}$ organic residues; and wherein $R_1$ and $R_2$ are different, or $R_1$ and $R_2$ may form a ring, and at least one of $R_1$ and $R_2$ is fluorinated; wherein fluorine is present at in an amount greater than 1 weight percent, but not more than 50 weight percent.

2. A compound according to claim 1, wherein $R_1$ or $R_2$ is formed from an alcohol independently selected from the group consisting of primary, secondary, tertiary or aromatic fluorinated alcohols and primary, secondary, tertiary or aromatic non-fluorinated alcohols, such that at least one of $R_1$ and $R_2$ is derived from a fluorinated alcohol.

3. A compound according to claim 2, wherein the fluorinated alcohol is selected from the group consisting of alcohols having the molecular formulae:

$F(CF_2)_xCH_2OH$ wherein x is from 1 to about 20.

$H(CF_2)_xCH_2OH$, wherein x is from 1 to about 20, $F(CF_2CF_2)_xCH_2CH_2OH$, wherein x is from 1 to about 10.

$F(CF_2CF_2)_x(CH_2CH_2O)_yOH$, wherein x is from 1 to about 10 and y is from 1 to about 20, and $F(CFCF_3 CF_2O)_xCF(CF_3)CH_2OH$, wherein x is from 1 to about 20.

4. A compound according to claim 3, wherein the fluorinated alcohol is selected from the group consisting of 1H, 1H-heptafluoro-1-butanol and 1H, 1H-perfluoro-1-octanol, 1H, 1H, 5H-octafluoro-1-pentanol and 1H, 1H, 2H, 2H-perfluoro-1-octanol.

5. A compound according to claim 4, wherein the fluorinated alcohol is 1H, 1H, 2H, 2H-perfluoro-1-octanol.

6. A compound according to claim 2, wherein either $R_1$ or $R_2$ is formed from a non-fluorinated alcohol selected from the group consisting of methanol, ethanol, n-propanol, isopropanol, n-butanol, isobutanol, t-butanol, 4-methyl-2-pentanol, 2-ethylhexanol, isotridecanol, cyclohexanol, cyclododecanol, phenol, cresol, higher alcohols and fatty alcohols.

7. A compound according to claim 1, which is a metallic salt comprising a metal atom selected from the group consisting of zinc, molybdenum, barium, aluminum, sodium, calcium, lithium, lead, tin, copper, cadmium, cobalt, strontium, nickel and combinations thereof.

8. A compound according to claim 1, wherein the metallic salt comprises a metal atom selected from the group consisting of zinc, molybdenum and combinations thereof.

9. A compound according to claim 1, wherein the metallic salt is zinc.

10. A compound of the formula (I) or metallic salts thereof:

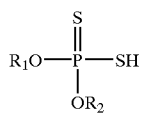

(I)

wherein $R_1$ and $R_2$ are each independently selected from the group consisting of $C_1$ to $C_{40}$ organic residues; and wherein $R_1$ and $R_2$ are the same or different, or $R_1$ and $R_2$ may form a ring, and at least one of $R_1$ and $R_2$ is a fluorinated $C_1$ to $C_{40}$ organic residue, provided that when $R_1$ and $R_2$ are the same, neither $R_1$ nor $R_2$ can be —$(CH_2(CF_2)_xCF_2H)$, where x is 1, 3 or 5; and wherein fluorine is present in an amount greater than 1 weight percent, but not more than 50 weight percent.

11. A lubricant composition comprising a lubricant base fluid and one or more compounds according to claim 1.

12. An anti-wear additive comprising one or more compounds of claim 1.

13. An anti-wear additive comprising a compound of formula (I) or metallic salts thereof:

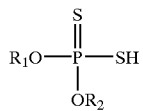

(I)

wherein $R_1$ and $R_2$ are each independently selected from the group consisting of $C_1$ to $C_{40}$ organic residues; and wherein at least one of $R_1$ and $R_2$ is a fluorinated $C_1$ to $C_{40}$ organic residue, and wherein fluorine is present in an amount greater than 1 weight percent, but not more than 50 weight percent.

14. An anti-wear additive according to claim 13, wherein the metallic salt is a compound of the formula (II):

$$[M^{x+}][S_2P(OR)_2]_x \quad (II)$$

wherein M is a metal atom and x is the valency of the metal atom; wherein the R groups are selected from $R_1$ and $R_2$, as defined above, provided that at least one or $R_1$ or $R_2$ is fluorinated.

15. A lubricant composition comprising a mineral oil base fluid and at least one fluorinated compound according to formula (I):

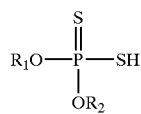

(I)

wherein at least one of $R_1$ and $R_2$ is a fluorinated $C_1$ to $C_{40}$ organic residue; and wherein $R_1$ and $R_2$ are the same or different, or $R_1$ and $R_2$ may form a ring, and wherein fluorine is present in an amount greater than 1 weight percent, but not more than 50 weight percent.

16. A lubricant composition according to claim 15, further comprising at least one fluorinated dialkyl dithiophosphate salt.

17. A lubricant composition according to claim 16, wherein the fluorinated dialkyl dithiophosphate salt is a compound according to formula (II):

$$[M^{x+}][S_2P(OR)_2]_x \quad (II)$$

wherein M is a metal atom and x is the valency of the metal atom;

wherein the R groups are selected from $R_1$ and $R_2$, as defined above, provided that at least one of $R_1$ or $R_2$ is fluorinated.

18. A formulated lubricant for use in internal combustion engines comprising a lubricant base fluid and at least one fluorinated compound according to claim 1, and optionally comprising one or more other additives selected from the group consisting of viscosity modifiers, oxidation inhibitors, pour point depressants, detergents, dispersants, friction modifiers, anti-wear agents, foam inhibitors, corrosion inhibitors and metal deactivators.

* * * * *